United States Patent [19]

Stinavage

[11] Patent Number: 5,700,834
[45] Date of Patent: Dec. 23, 1997

[54] SYNERGISTIC ANTIMICROBIAL COMPOSITION OF 1,2-DIBROMO-2,4-DICYANOBUTANE AND ALKYLGUANIDINE COMPOUNDS

[75] Inventor: Paul Stinavage, New Market, Md.

[73] Assignee: Calgon Corporation, Pittsburgh, Pa.

[21] Appl. No.: 521,698

[22] Filed: Aug. 31, 1995

(Under 37 CFR 1.47)

[51] Int. Cl.$^6$ .................... A01N 37/34; A01N 37/52
[52] U.S. Cl. .................................. 514/526; 514/634
[58] Field of Search ............................ 514/526, 634

[56] References Cited

U.S. PATENT DOCUMENTS

| | | | |
|---|---|---|---|
| 2,867,562 | 1/1959 | Lamb | 167/22 |
| 2,906,595 | 9/1959 | Pelcak et al. | 21/2.7 |
| 3,116,326 | 12/1963 | Lamb | 260/564 |
| 3,142,615 | 7/1964 | Wehner | 167/22 |
| 3,143,459 | 8/1964 | Marks et al. | 167/42 |
| 3,264,172 | 8/1966 | Regutti | 162/161 |
| 3,628,941 | 12/1971 | Marks | 71/67 |
| 3,644,380 | 2/1972 | Harmetz et al. | 260/294.9 |
| 3,833,731 | 9/1974 | Grier et al. | 424/304 |
| 3,833,743 | 9/1974 | Morse et al. | 426/195 |
| 3,873,597 | 3/1975 | Harmetz et al. | 424/304 |
| 3,877,922 | 4/1975 | Grier et al. | 71/67 |
| 3,929,858 | 12/1975 | Swigert | 260/465.7 |
| 4,442,122 | 4/1984 | Engelhart et al. | 424/304 |
| 4,496,581 | 1/1985 | Engelhart et al. | 514/438 |
| 4,830,657 | 5/1989 | Jakubowski et al. | 71/67 |
| 5,034,405 | 7/1991 | Jakubowski | 514/369 |
| 5,124,355 | 6/1992 | Tully et al. | 514/526 |
| 5,364,874 | 11/1994 | Morpeth | 514/373 |
| 5,444,088 | 8/1995 | Syrinek | 514/526 |

*Primary Examiner*—Allen J. Robinson
*Attorney, Agent, or Firm*—Diane R. Meyers; William C. Mitchell

[57] ABSTRACT

Synergistic antimicrobial combinations comprising 1,2-dibromo-2,4-dicyanobutane and an alkylguanidine compound, preferably dodecylguanidine hydrochloride, are disclosed. Methods for inhibiting microbial growth using these synergistic antimicrobial combinations are also disclosed.

13 Claims, No Drawings

SYNERGISTIC ANTIMICROBIAL COMPOSITION OF 1,2-DIBROMO-2,4-DICYANOBUTANE AND ALKYLGUANIDINE COMPOUNDS

BACKGROUND OF THE INVENTION

1. Field of the Invention

The present invention relates to synergistic antimicrobial compositions which are generally useful for inhibiting microbial growth wherever such microbial growth is found, e.g. in aqueous systems related to a wide variety of industrial applications. More particularly, the present invention relates to synergistic admixtures of 1,2-dibromo-2,4-dicyanobutane (DBDCB) and alkylguanidine compounds. Methods for using the same are also disclosed.

2. Description of the Background Art

Both 1,2-dibromo-2,4-dicyanobutane (DBDCB), also known as 2-bromo-2-bromomethylglutaronitrile, and alkylguanidine compounds, such as dodecylguanidine hydrochloride (DGH), are known individually as antimicrobial agents. The unexpected finding of the present invention is that they are synergistic when used in combination. As used herein, the terms "synergy" and "synergistic" refer to instances where the effectiveness of a composition comprising two or more biocides, such as DBDCB and DGH, exceeds the sum of the efficacies of the individual components taken alone. Thus, using a synergistic biocidal combination may allow for use of a lower overall concentration of biocide or the realization of an enhanced antimicrobial effect at a comparable dosage.

U.S. Pat. Nos. 3,833,731, 3,877,922, 3,873,597, 3,644,380, 3,833,743, and 3,929,858 disclose DBDCB and its use as an antibacterial, antifungal, and algicidal agent. Compounds related to DBDCB are also effective as antimicrobial agents. For example, U.S. Pat. No. 4,442,122 describes the use of 1,2-dibromo-2-cycloalkane compounds to inhibit microbial growth, and U.S. Pat. No. 4,496,581 discloses 1,2-dibromo-2-cyano-2-(heterocyclic) alkane compounds and their use as antimicrobial agents.

The use of DBDCB and related compounds in conjunction with other antimicrobial agents is also known in the art. U.S. Pat. No. 4,830,657 describes a synergistic antimicrobial combination comprising DBDCB and 1,2-benzisothiazolin-3-one. U.S. Pat. No. 5,034,405 discloses use of admixtures of DBDCB, 2-methyl-4-isothiazolin-3-one and 5-chloro-2-methyl-4-isothiazolin-3-one as antimicrobial agents. U.S. Pat. No. 5,124,355 discloses an antimicrobial composition of DBDCB and 2-(decylthio) ethaneamine and a method of using the same. U.S. Pat. No. 5,364,874 discloses the antibacterial and antifungal activity of 2-halo-2-halomethylglutaronitriles, including DBDCB, and 4,5-polymethylene-4-isothiazolin-3-one.

Likewise, alkylguanidine compounds, including dodecylguanidine hydrochloride, are known for their antimicrobial properties. For example, mineral acid or monocarboxylic acid salts of alkylguanidines and their use as antimicrobial agents are disclosed in U.S. Pat. Nos. 2,867,562, 2,906,595, 3,116,326, 3,142,615, 3,143,459, 3,264,172, and 3,628,941. The acid salts of dodecylguanidine are the best known and widely used compounds of the class.

As used herein, the phrases "antimicrobial", "biocide", and "inhibiting microbial growth" refer to agents useful for the killing of, the inhibition of, or the control of the growth of bacteria, yeast, fungi, and/or algae. A number of important industries have experienced serious adverse effects from the activity of such biological growth on the raw materials which they employ, in their process waters, on various components of their manufacturing processes, and in the finished products which they produce. Such industries include the paint, wood, textile, cosmetic, leather, tobacco, fur, rope, paper, pulp, plastics, fuel, oil, rubber, and machine industries.

It is contemplated that the synergistic admixture of DBDCB and alkylguanidine compounds as disclosed herein, and the methods for using the same, will be useful in virtually any aqueous system or on any article of manufacture in which inhibition of microbial growth is desired, absent compatibility problems. Important applications of the synergistic antimicrobial combinations of the present invention include, for example: inhibiting the growth of bacteria and fungi in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms; protecting paint films, especially exterior paints, from attack from fungi which occurs during weathering of the paint film; protecting processing equipment from slime deposits during manufacture of cane and beet sugar; preventing microorganism buildup and deposits in air washer or scrubber systems and in industrial fresh water supply systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing and which are susceptible to degradation by microorganisms during storage and transport; as a hard surface disinfectant to prevent growth of bacteria and fungi on walls, floors, etc.; in swimming pools to prevent algal growth; and to control bacterial and fungal growth in various cosmetic products.

The synergistic antimicrobial composition disclosed in the present invention is particularly applicable to slime control in papermaking processes. The control of bacteria and fungi in pulp and paper mill water systems which contain aqueous dispersions of papermaking fibers in various consistencies is especially important. The uncontrolled buildup of slime produced by the accumulation of bacteria and fungi causes off-grade production, decreased production due to down-time and greater cleanup frequency, increased raw material usage, and increased maintenance costs. The problem of slime deposits is especially critical in light of the widespread use of closed white water systems in the paper industry.

Another important area in which the antimicrobial compositions of the present invention are particularly useful is in the control of bacterial and fungal growth in clay and pigment slurries. These slurries comprise various clays (e.g., kaolin) and pigments (e.g., calcium carbonate and titanium dioxide) and usually are manufactured at a location separate from the end use application. This means that they are generally transported and stored for later use at the application site. Because of high quality standards for the paper and paint products in which such slurries are used, it is essential that these clay or pigment slurries have a very low microorganism count.

In addition, the synergistic combination of the present invention and methods of using the same have been found especially useful in controlling the harmful effects of microorganisms in water or aqueous media. Systems which utilize circulating water or aqueous media become infected with microorganisms and experience substantial impairment of their efficiency when deposits of the microorganisms build up in the system. The deposits coat the walls of tanks and other vessels and any machinery or processing equipment which is employed and create blockages in pipes and valves. The deposits also create discolorations and other imperfections in the products being produced, forcing costly shutdowns. Control of microorganisms in aqueous media is particularly important where there are dispersed particles or fines in the aqueous media, e.g., dispersed cellulosic fibers and dispersed fillers and pigments in papermaking, and dispersed pigments in paint manufacture.

Accordingly, there remains a very real and substantial need for antimicrobial compositions capable of effectively controlling and/or inhibiting microbial growth in industrial aqueous systems and in articles of manufacture. Because of increasing environmental regulations, there is still a further need to provide biocidal compositions having enhanced antimicrobial effect which are effective in lower doses than historically used. Use of lower amounts of biocides has a favorable impact on the environment, and allows users to realize significant cost savings.

SUMMARY OF THE INVENTION

The present invention generally meets the above described needs by providing synergistic antimicrobial combinations comprising 1,2-dibromo-2,4-dicyanobutane (DBDCB) and alkylguanidine compounds, particularly dodecylguanidine hydrochloride (DGH). The present invention also provides a method for inhibiting microbial growth in aqueous systems and on articles of manufacture prone to such growth comprising adding to said systems or applying to said articles an effective amount of a DBDCB and alkylguanidine composition.

As used herein, the term "effective amount" refers to that amount of a composition comprising DBDCB and an alkylguanidine compound necessary to achieve the desired level of inhibition or control of microbial growth in the aqueous system or on the article being treated.

DESCRIPTION OF THE INVENTION

The present invention is directed to a synergistic antimicrobial composition comprising: a) 1,2-dibromo-2,4-dicyanobutane (DBDCB); and b) an alkylguanidine compound, wherein the weight ratio of a) to b), on an active basis, ranges from about 1000:1 to 1:1000. The preferred alkylguanidine compound is dodecylguanidine hydrochloride (DGH). The present invention is further directed to a method for inhibiting microbial growth in an aqueous system or on an article of manufacture prone to such growth, which method comprises treating said system or said article with an effective amount of an antimicrobial combination of: a) DBDCB and b) an alkylguanidine compound, wherein the weight ratio of a) to b), on an active basis, ranges from about 1000:1 to 1:1000. As used herein, the term "alkylguanidine compound" refers to any of the mineral acid salts, monocarboxylic acid salts, or other salts of alkyl guanide including but not limited to the salts of dodecylguanidine.

In accordance with the present invention, the weight ratio of the two components of the synergistic combination are dictated by the dosage levels of each component which demonstrate synergism, based on 100% active ingredient, relative to each end use application. Typically, the weight ratio of component a), DBDCB, and component b), for example DGH, ranges from about 1000:1 to 1:1000 on an active basis, preferably from about 100:1 to 1:100, more preferably from about 25:1 to 1:25. As will be understood by one skilled in the art, however, the synergistic weight ratio of the two components generally varies to some extent depending on the application and the organism being controlled. For example, a higher ratio of DBDCB to DGH might be more effective in one application, while a higher ratio of DGH to DBDCB might be more effective in another application. The DBDCB/DGH composition has been found particularly effective against bacteria when used in a weight ratio of between about 25:1 and 1:25.

An effective amount of a synergistic combination of DBDCB and DGH should be added to the aqueous system being treated. At least 0.1 parts per million (ppm), based on the weight of water in the system being treated, of the synergistic combination described above is added. Preferably, between about 0.5 ppm and about 500 ppm of DBDCB and between about 0.5 ppm and 125 ppm of DGH, based on the weight of water in the system being treated, are added. More preferably, between about 2 ppm and 250 ppm of DBDCB and between about 10 ppm and 50 ppm of DGH, based on the weight of water in the system being treated, are added. It is well within the ordinary skill of one practicing in the art to determine the effective amount of biocide for a given system based on various system parameters including but not limited to the size of the system, pH of the system, the types of organisms present and the amount of control desired.

Likewise, an effective amount of a synergistic combination of DBDCB and DGH should be applied to the article of manufacture being treated. Generally, a solution of the synergistic antimicrobial combination described above having a concentration of at least 0.1 ppm is incorporated into, sprayed onto, used to dip, or otherwise applied to the substrate being treated in order to prevent growth of bacteria, fungi, yeast and algae. Again, it is well within the ordinary skill of one practicing in the art to determine the effective amount of biocide to apply to a given article of manufacture being treated.

The active ingredients of the synergistic antimicrobial compositions of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the synergistic antimicrobial combinations are liquid, they may be employed neat or may be incorporated into various formulations, both solid and liquid, as an adsorbate on suitable inert carriers such as talc, clays, diatomaceous earth and the like, or water and various organic liquids such as lower alkanols, kerosene, benzene, toluene, and other petroleum distillate fractions or mixtures thereof. DBDCB is commercially available in wet cake, dry powder and aqueous dispersion form from Calgon Corporation, Pittsburgh, Pa. DGH is also commercially available from Calgon Corporation in liquid form.

It will also be understood by one skilled in the art that the synergistic antimicrobial combination disclosed herein may be used in combination with other antimicrobial materials. For example, the combination can be combined with other fungicides and bactericides in appropriate concentrations and in appropriate instances so as to combine the action of each to obtain particularly useful results. Such combinations might find particular application in the preparation of germicidal soaps, in the production of cosmetics and aqueous coatings and in combating paper mill slime accumulations. It is quite clear also that the synergistic antimicrobial combination of the present invention can be combined with other algicidal agents as well.

In accordance with the present invention there is still further provided a method of inhibiting the growth of at least one of: bacteria, yeast, fungi and algae. According to the methods of the present invention, this growth is inhibited in aqueous systems or on articles of manufacture prone to such growth. These methods comprise adding to the aqueous system or treating the article containing said bacteria, yeast, fungi and/or algae with an effective amount of a synergistic combination of DBDCB and an alkylguanidine compound such as DGH. This addition can be accomplished either by simple addition of DBDCB and DGH together as a single admixture, or by addition of the two components separately. Such separate administration can either be at the same time or at different times. The net effect will be the same—the system or article being treated will ultimately have incorporated therein or have applied thereto the desired dosage concentration of each component.

Further, the compositions of the present invention are believed to be effective irrespective of the method of application. For example, the antimicrobial compositions desired herein can be added to a system being treated via a low level, continuous feed practice, a semi-continuous feed practice or through slug feeding. All of these feeding practices will be familiar to one having ordinary skill in the art. Slug feeding is particularly effective and therefore is a preferred manner of employing the methods of the present invention. This type of feed allows the user to monitor the microorganism concentration in the system and feed product only when microorganism concentrations increase. The user realizes a cost savings by feeding an effective amount of DBDCB and DGH only when needed.

As noted above, the present invention is based upon the discovery that use of DBDCB in conjunction with alkylguanidine compounds produces synergistic results and is effective in controlling the growth of bacteria, yeast, fungi and algae in a variety of industrial and other applications. The utility of the synergistic antimicrobial combination disclosed herein derives from its versatility both in the numerous industries in which it can be applied, as well as the numerous microorganisms against which it is effective. In particular, the large economic losses in papermaking operations caused by the accumulation of bacterial and fungal slimes in various parts of the system can be eliminated to a significant extent by use of the synergistic combination described herein.

The superior antimicrobial activity of the synergistic antimicrobial combination of DBDCB and DGH has been confirmed using standard laboratory techniques. The antimicrobial combination has been found effective, for example, in inhibiting bacterial growth including but not limited to *Klebsiella pneumoniae* and *Escherichia coli* and has been found to be particularly effective against *Pseudomonas aeruginosa*.

EXAMPLES

The following examples are set forth to illustrate the present invention and should not be construed as limiting the invention in any way.

EXAMPLE I

The following example shows the biocidal efficacy in a microtiter test of the antimicrobial composition of the present invention. Three different bacterial strains, as well as a mixture of all three of the strains, were used in this example as indicated below:

*Klebsiella pneumoniae*

*Bacillus megaterium*

*Pseudomonas aeruginosa*

Mix of all three bacteria

Each of the three bacteria were separately grown on Standard Method Ager (STM) plates and incubated at 37° C. for a period of between about 24–48 hours. The bacteria were then swabbed from their respective STM plates and suspended in 50 ml of double strength nutrient broth (2XNB) and incubated again at 37° C. for 24 hours; each organism was incubated in a separate tissue culture flask. The 2XNB was prepared by mixing about 16 grams of nutrient broth powder in about 1000 ml of deionized water which had been autoclave sterilized. Following the 24 hour incubation of each of the organism suspensions, the suspensions were diluted in a ratio of 1:10 with additional 2XNB. Samples from each of these diluted cultures were then used in the microtiter test. To prepare the mix of all three of the organisms, an equal amount, approximately 10 ml, of each of the diluted cultures was mixed together in a separate tissue culture flask. Samples from this mixture were then used in the microtiter test.

An 8X stock solution of DBDCB was prepared by dissolving about 4.0 grams of 20% active DBDCB in about 5 ml of methanol and diluting with about 100 ml of deionized water. The DBDCB used in the examples was obtained from Calgon Corporation, Pittsburgh, Pa., as Metasol® CB-220 (20% DBDCB). A DBDCB 4X stock solution was prepared by diluting the 8X stock solution in a 1:1 ratio with deionized water. A DGH 4X stock solution was prepared by adding about 1.6 grams of about 25% active DGH to about 100 ml of deionized water and mixing until dissolved. The DGH was obtained from Calgon Corporation, Pittsburgh, Pa. as Metasol® 600HF (24.7% DGH).

Six microtiter plates were initially prepared for use in the example, each microtiter plate having 8 rows, A–H, and 12 columns, 1–12. All of the wells of rows A–H of column 1 contained the same amount of biocide; likewise, the wells of rows A–H of column 2 contained the same amount of biocide, and so on through the wells of column 10. These amounts are depicted below in Table 1.

TABLE 1

| AMOUNT OF EACH BIOCIDE IN WELLS OF MICROTITER PLATES 1–6 | | | | | | | | | | | | |
|---|---|---|---|---|---|---|---|---|---|---|---|---|
| | | COLUMN CONCENTRATIONS (ppm Active) | | | | | | | | | | |
| PLATE # | BIOCIDE | 1 | 2 | 3 | 4 | 5 | 6 | 7 | 8 | 9 | 10 | 11 | 12 |
| 1 | DBDCB | 1000 | 500 | 250 | 125 | 62.5 | 31.3 | 15.6 | 7.8 | 3.9 | 1.95 | − | + |
| | DGH | 0 | 0 | 0 | 0 | 0 | 0 | 0 | 0 | 0 | 0 | − | + |
| 2 | DBDCB | 0 | 0 | 0 | 0 | 0 | 0 | 0 | 0 | 0 | 0 | − | + |
| | DGH | 1000 | 500 | 250 | 125 | 62.5 | 31.3 | 15.6 | 7.8 | 3.9 | 1.95 | − | + |
| 3 | DBDCB | 1000 | 500 | 250 | 125 | 62.5 | 31.3 | 15.6 | 7.8 | 3.9 | 1.95 | − | + |
| | DGH | 100 | 100 | 100 | 100 | 100 | 100 | 100 | 100 | 100 | 100 | − | + |

TABLE 1-continued

AMOUNT OF EACH BIOCIDE IN WELLS OF MICROTITER PLATES 1-6

| PLATE # | BIOCIDE | COLUMN CONCENTRATIONS (ppm Active) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| 4 | DBDCB | 1000 | 500 | 250 | 125 | 62.5 | 31.3 | 15.6 | 7.8 | 3.9 | 1.95 | – | + |
| | DGH | 50 | 50 | 50 | 50 | 50 | 50 | 50 | 50 | 50 | 50 | – | + |
| 5 | DBDCB | 1000 | 500 | 250 | 125 | 62.5 | 31.3 | 15.6 | 7.8 | 3.9 | 1.95 | – | + |
| | DGH | 25 | 25 | 25 | 25 | 25 | 25 | 25 | 25 | 25 | 25 | – | + |
| 6 | DBDCB | 1000 | 500 | 250 | 125 | 62.5 | 31.3 | 15.6 | 7.8 | 3.9 | 1.95 | – | + |
| | DGH | 10 | 10 | 10 | 10 | 10 | 10 | 10 | 10 | 10 | 10 | – | + |

As is illustrated in the table above, the amount of DBDCB in the wells of plate 1 and the amount of DGH in the wells of plate 2 were varied in a ladder series ranging from 1000 ppm active to 1.95 ppm active; plate 1 represented use of DBDCB alone, while plate 2 represented the use of DGH alone. Plates 1 and 2 were used to determine the minimum amount of each biocide which, when used alone, would inhibit microbial growth. Plates 3–6 were used to determine the concentrations at which the antimicrobial combination of the present invention was effective. As in Plate 1, the amount of DBDCB in Plates 3–6 was varied in a ladder series ranging from 1000 ppm to 1.95 ppm active. The DGH in Plates 3–6 was held constant at a different concentration for each plate as indicated in the table above. No biocide was added to the wells of column 12 in any of the plates, which represented an organism control, or positive control. This positive control was run to ensure that the organisms were capable of growing in the environment provided. No bacteria were added to the wells of column 11 in any of the plates, which represented a broth control, or a negative control. This was done to ensure that there was no contamination of the plates. In each of the 6 microtiter plates *Pseudomonas aeruginosa* was added to rows A and B, *Bacillus megaterium* to rows C and D, *Klebsiella pneumoniae* to rows E and F, and the mix of all three bacteria to rows G and H.

Plates 1 and 2 were set up as follows: for plate 1, 100 microliters of sterile deionized water were added to all of the wells. 100 microliters of 4X DBDCB stock were added to the wells of column 1. Each of the wells of column 1 were mixed individually; 100 microliters of the biocide/water mixture of the wells of column 1 were then transferred to the wells of column 2. This serial dilution was continued down to column 10. 100 microliters of 2XNB containing the appropriate bacteria were added to the wells of columns 1–10 and 12 as indicated above. The same procedure was repeated for plate 2, but using the 4X DGH stock solution rather than the 4X DBDCB stock solution. 100 microliters of 2XNB were added to the column 11 wells of both plates 1 and 2.

Plates 3–6 were set up as follows: 50 microliters of sterile deionized water were added to all of the wells. 50 microliters of 8X DBDCB stock solution were added to the column 1 wells of all of plates 3–6. Each of the wells of column 1 were mixed individually; 50 microliters of the deionized water/8X DBDCB stock solution were then transferred from the column 1 wells to the column 2 wells. This serial dilution was continued down to column 10. 50 microliters of the appropriate DGH stock solution were added to all the wells in columns 1–10 for plates 3–6. A 100 ppm active DGH solution was used for plate 3, a 50 ppm active DGH solution for plate 4, a 25 ppm active DGH solution for plate 5, and a 10 ppm active DGH solution for plate 6. Upon addition of the DGH stock solution, all of the wells were subject to mixing. 50 microliters of 2XNB were added to the wells of column 11; 100 microliters of the appropriate 2XNB bacterial suspension, as indicated above, were added to all of the remaining wells. Plates 3–6 were used to determine the minimum inhibitory concentration (MIC) for each biocide combination against each bacteria strain. The MIC is the least amount of biocide needed to prevent growth in the well, with growth being defined as a turbidity or a "button" of cells at the bottom of the well.

Plates 1–6 were then subcultured at 1 hour following biocide addition. Ten microliters of the biocide/bacteria mixture in each well of plates 1–6 for columns 1–10, and the control mixture for columns 11–12, were transferred to the respective wells of six additional plates, the wells of which contained 100 microliters of sterile 1XNB. Subculturing was performed again by the same procedure at 3, 5 and 24 hours following biocide addition. Subculturing was done to determine the minimum biocidal concentration (MBC). The MBC is the lowest concentration of biocide that results in no growth after subculturing and subsequent incubation; here, the subculturing occurred at 4 different times and the subcultured organisms incubated for an additional 24 hours at 37° C.

All of the microtiter plates including the MIC plates and the MBC plates were incubated for 24 hours at 37° C. Following the 24 hour incubation period, the presence or absence of growth in each well of the MBC plates was determined. Growth in the microtiter plates was determined with a Dynatech MR-5000 microplate reader, available from Dynatech Laboratories, Chantilly, Va., the use of which will be familiar to one having ordinary skill in the art. The presence or absence of growth in each well, along with the concentration of biocide in each well, was then used to determine the synergistic properties of the biocide combinations. The synergistic properties were evaluated by determining the Kull value, or K value; the K value was determined for each of the bacteria tested in the MBC plates. The method for calculating K value is well known to those skilled in the art. In this example, the K value was determined by the following formula:

$$K = \frac{[DBDCB] \text{ In Combination}}{[DBDCB] \text{ Alone}} + \frac{[DGH] \text{ In Combination}}{[DGH] \text{ Alone}}$$

where "[DBDCB] In Combination" means the concentration of DBDCB which, when used in combination with DGH, resulted in inhibition of microbial growth;

"[DGH] In Combination" means the concentration of DGH which, when used in combination with DBDCB, resulted in inhibition of microbial growth;

"[DBDCB] Alone" means the concentration of DBDCB which, when used alone, resulted in inhibition of microbial growth; and "[DGH] Alone" means the concentration of the DGH which, when used alone, resulted in inhibition of microbial growth. A K value of less than 1 indicates synergy between the two biocides, a K value of greater than 1 indicates antagonism between the two biocides, and a K value equal to 1 indicates an additive effect of the two biocides.

The K values determined for each of the organisms used in the example are recorded in Tables 2 through 4. The 24 hour subculture plates provided inconclusive results.

*Escherichia coli*
*Pseudomonas aeruginosa*
Mix of all three bacteria

The organisms were subcultured after 2,4 and 24 hours. The presence or absence of growth in the wells of both the

TABLE 2

"K" VALUES OF ONE HOUR PLATES

| Organism | [DBDCB] Alone, ppm | [DGH] Alone, ppm | [DBDCB] In Combination, ppm | [DGH] In Combination, ppm | K Value | Weight Ratio |
| --- | --- | --- | --- | --- | --- | --- |
| *Pseudomonas aeruginosa* | 1000 | 500 | 63 | 25 | 0.113 | 2.5:1 |
| *Bacillus megaterium* | 2 | 2 | 2 | 25 | 13.5 | — |
| *Klebsiella pneumoniae* | 500 | 125 | 2 | 25 | 0.2 | 1:12.5 |
| Mixture of above three | 500 | 125 | 16 | 25 | 0.232 | 1:1.5 |

TABLE 3

"K" VALUES OF THREE HOUR PLATES

| Organism | [DBDCB] Alone, ppm | [DGH] Alone, ppm | [DBDCB] In Combination, ppm | [DGH] In Combination, ppm | K Value | Weight Ratio |
| --- | --- | --- | --- | --- | --- | --- |
| *Pseudomonas aeruginosa* | 500 | 125 | 250 | 10 | 0.58 | 25:1 |
| *Bacillus megaterium* | 2 | 2 | 2 | 10 | 6 | — |
| *Klebsiella pneumoniae* | 250 | 31 | 2 | 10 | 0.3306 | 1:5 |
| Mixture of above three | 500 | 63 | 125 | 10 | 0.41 | 12.5:1 |

TABLE 4

"K" VALUES OF FIVE HOUR PLATES

| Organism | [DBDCB] Alone, ppm | [DGH] Alone, ppm | [DBDCB] In Combination, ppm | [DGH] In Combination, ppm | K Value | Weight Ratio |
| --- | --- | --- | --- | --- | --- | --- |
| *Pseudomonas aeruginosa* | 500 | 125 | 250 | 10 | 0.58 | 25:1 |
| *Bacillus megaterium* | 2 | 2 | 2 | 10 | 6 | — |
| *Klebsiella pneumoniae* | 125 | 31 | 2 | 10 | 0.3386 | 1:5 |
| Mixture of above three | 250 | 63 | 125 | 10 | 0.66 | 12.5:1 |

As can be seen from the results of Tables 2–4, synergy was demonstrated against both *Pseudomonas aeruginosa* and *Klebsiella pneumoniae*, as well as the mix of these two organisms with *Bacillus megaterium*.

EXAMPLE II

The above example was repeated using the following organisms:
*Klebsiella pneumoniae*

MIC and MBC plates was determined. All other test methods and conditions were as recited in Example I.

The K values determined for each of the plates used in the example are recorded in Tables 5 through 8.

TABLE 5

"K" VALUES OF MIC PLATES

| Organism | [DBDCB] Alone, ppm | [DGH] Alone, ppm | [DBDCB] In Combination, ppm | [DGH] In Combination, ppm | K Value |
| --- | --- | --- | --- | --- | --- |
| *Pseudomonas aeruginosa* | 250 | 125 | 23.4 | 100 | 0.89 |
| *Pseudomonas aeruginosa* | 250 | 125 | 62.5 | 50 | 0.65 |
| *Pseudomonas aeruginosa* | 250 | 125 | 93.8 | 25 | 0.58 |
| *Pseudomonas aeruginosa* | 250 | 125 | 125 | 10 | 0.58 |

TABLE 5-continued

"K" VALUES OF MIC PLATES

| Organism | [DBDCB] Alone, ppm | [DGH] Alone, ppm | [DBDCB] In Combination, ppm | [DGH] In Combination, ppm | K Value |
| --- | --- | --- | --- | --- | --- |
| Escherichia coli | 31.2 | 3.9 | 1.95 | 100 | 25.7 |
| Escherichia coli | 31.2 | 3.9 | 1.95 | 50 | 12.9 |
| Escherichia coli | 31.2 | 3.9 | 1.95 | 25 | 6.5 |
| Escherichia coli | 31.2 | 3.9 | 1.95 | 10 | 2.6 |
| Klebsiella pneumoniae | 31.2 | 5.8 | 1.95 | 100 | 17.3 |
| Klebsiella pneumoniae | 31.2 | 5.8 | 1.95 | 50 | 8.7 |
| Klebsiella pneumoniae | 31.2 | 5.8 | 1.95 | 25 | 4.4 |
| Klebsiella pneumoniae | 31.2 | 5.8 | 1.95 | 10 | 1.8 |
| Mixture of above three | 125 | 125 | 31.2 | 100 | 1.0 |
| Mixture of above three | 125 | 125 | 46.8 | 50 | 0.77 |
| Mixture of above three | 125 | 125 | 125 | 25 | 1.2 |
| Mixture of above three | 125 | 125 | 125 | 10 | 1.1 |

TABLE 6

"K" VALUES OF TWO HOUR PLATES

| Organism | [DBDCB] Alone, ppm | [DGH] Alone, ppm | [DBDCB] In Combination, ppm | [DGH] In Combination, ppm | K Value |
| --- | --- | --- | --- | --- | --- |
| Pseudomonas aeruginosa | 250 | 125 | 31.2 | 100 | 0.92 |
| Pseudomonas aeruginosa | 250 | 125 | 78.1 | 50 | 0.71 |
| Pseudomonas aeruginosa | 250 | 125 | 62.5 | 25 | 0.45 |
| Pseudomonas aeruginosa | 250 | 125 | 125 | 10 | 0.58 |
| Escherichia coli | 250 | 78.1 | 1.95 | 100 | 12.8 |
| Escherichia coli | 250 | 78.1 | 2.9 | 50 | 0.65 |
| Escherichia coli | 250 | 78.1 | 2.9 | 25 | 0.33 |
| Escherichia coli | 250 | 78.1 | 11.7 | 10 | 0.17 |
| Klebsiella pneumoniae | 125 | 15.6 | 1.95 | 100 | 6.4 |
| Klebsiella pneumoniae | 125 | 15.6 | 1.95 | 50 | 3.2 |
| Klebsiella pneumoniae | 125 | 15.6 | 1.95 | 25 | 1.6 |
| Klebsiella pneumoniae | 125 | 15.6 | 1.95 | 10 | 0.66 |
| Mixture of above three | 125 | 125 | 62.5 | 100 | 1.3 |
| Mixture of above three | 125 | 125 | 46.8 | 50 | 0.77 |
| Mixture of above three | 125 | 125 | 125 | 25 | 1.2 |
| Mixture of above three | 125 | 125 | 93.8 | 10 | 0.83 |

TABLE 7

"K" VALUES OF FOUR HOUR PLATES

| Organism | [DBDCB] Alone, ppm | [DGH] Alone, ppm | [DBDCB] In Combination, ppm | [DGH] In Combination, ppm | K Value |
| --- | --- | --- | --- | --- | --- |
| Pseudomonas aeruginosa | 250 | 187.5 | 23.4 | 100 | 0.63 |
| Pseudomonas aeruginosa | 250 | 187.5 | 62.5 | 50 | 0.52 |
| Pseudomonas aeruginosa | 250 | 187.5 | 62.5 | 25 | 0.38 |
| Pseudomonas aeruginosa | 250 | 187.5 | 125 | 10 | 0.55 |
| Escherichia coli | 125 | 15.6 | 1.95 | 100 | 6.4 |
| Escherichia coli | 125 | 15.6 | 1.95 | 50 | 3.2 |
| Escherichia coli | 125 | 15.6 | 1.95 | 25 | 1.6 |
| Escherichia coli | 125 | 15.6 | 1.95 | 10 | 0.66 |
| Klebsiella pneumoniae | 62.5 | 5.8 | 1.95 | 100 | 17.3 |
| Klebsiella pneumoniae | 62.5 | 5.8 | 1.95 | 50 | 8.6 |
| Klebseilla pneumoniae | 62.5 | 5.8 | 1.95 | 25 | 4.3 |
| Klebseilla pneumoniae | 62.5 | 5.8 | 1.95 | 10 | 1.8 |
| Mixture of above three | 125 | 125 | 46.8 | 100 | 1.2 |
| Mixture of above three | 125 | 125 | 46.8 | 50 | 0.77 |
| Mixture of above three | 125 | 125 | 62.5 | 25 | 0.70 |
| Mixture of above three | 125 | 125 | 125 | 10 | 1.1 |

TABLE 8

"K" VALUES OF TWENTY FOUR HOUR PLATES

| Organism | [DBDCB] Alone, ppm | [DGH] Alone, ppm | [DBDCB] In Combination, ppm | [DGH] In Combination, ppm | K Value |
|---|---|---|---|---|---|
| *Pseudomonas aeruginosa* | 250 | 250 | 46.8 | 100 | 0.59 |
| *Pseudomonas aeruginosa* | 250 | 250 | 93.8 | 50 | 0.58 |
| *Pseudomonas aeruginosa* | 250 | 250 | 93.8 | 25 | 0.48 |
| *Pseudomonas aeruginosa* | 250 | 250 | 125 | 10 | 0.54 |
| *Escherichia coli* | 31.2 | 3.9 | 1.95 | 100 | 25.7 |
| *Escherichia coli* | 31.2 | 3.9 | 1.95 | 50 | 12.9 |
| *Escherichia coli* | 31.2 | 3.9 | 32.2 | 25 | 7.4 |
| *Escherichia coli* | 31.2 | 3.9 | 1.95 | 10 | 2.6 |
| *Klebsiella pneumoniae* | 62.5 | 66.4 | 1.95 | 100 | 1.54 |
| *Klebsiella pneumoniae* | 62.5 | 66.4 | 1.95 | 50 | 0.78 |
| *Klebsiella pneumoniae* | 62.5 | 66.4 | 16.6 | 25 | 0.64 |
| *Klebsiella pneumoniae* | 62.5 | 66.4 | 1.95 | 10 | 0.18 |
| Mixture of above three | 250 | 250 | 46.8 | 100 | 0.59 |
| Mixture of above three | 250 | 250 | 62.4 | 50 | 0.45 |
| Mixture of above three | 250 | 250 | 125 | 25 | 0.60 |
| Mixture of above three | 250 | 250 | 125 | 10 | 0.54 |

As can be seen from the results of Tables 5–8, synergy was demonstrated against all of the organisms tested, including the mixture of all three of the organisms.

What is claimed is:

1. A synergistic antimicrobial combination comprising synergistic effective amounts of:
   a) 1,2-dibromo-2,4-dicyanobutane; and
   b) dodecylguanidine hydrochloride, wherein the weight ratio of a) to b), on an active basis, ranges between about 1000:1 and 1:1000.

2. The combination of claim 1 wherein the weight ratio of a) to b) ranges between about 25:1 and 1:25.

3. A method for inhibiting microbial growth in an aqueous system which comprises adding to said system an effective amount of a synergistic antimicrobial combination comprising:
   a) 1,2-dibromo-2,4-dicyanobutane; and
   b) dodecylguanidine hydrochloride, wherein the weight ratio of a) to b), on an active basis, ranges between about 1000:1 and 1:1000.

4. The method of claim 3 wherein the weight ratio of a) to b) ranges between about 25:1 and 1:25.

5. The method of claim 3 wherein the 1,2-dibromo-2,4-dicyanobutane and dodecylguanidine hydrochloride are added together as a single composition to the system being treated.

6. The method of claim 3 wherein the 1,2-dibromo-2,4-dicyanobutane and dodecylguanidine hydrochloride are added separately to the system being treated.

7. The method of claim 3 wherein at least 0.1 ppm of the synergistic antimicrobial composition is added to the system being treated.

8. The method of claim 4 wherein between about 2 ppm and 250 ppm 1,2-dibromo-2,4-dicyanobutane and between about 10 ppm and 50 ppm dodecylguanidine hydrochloride are added to the system being treated.

9. A method of inhibiting microbial growth on an article of manufacture which comprises applying to said article an effective amount of a synergistic antimicrobial combination comprising:
   a) 1,2-dibromo-2,4-dicyanobutane; and
   b) an alkylguanidine compound; wherein the weight ratio of a) to b), on an active basis, ranges between about 1000:1 and 1:1000.

10. The method of claim 9 wherein the weight ratio of a) to b) ranges between about 25:1 and 1:25.

11. The method of claim 9 wherein the 1,2-dibromo-2,4-dicyanobutane and dodecylguanidine hydrochloride are applied together as a single composition to the article being treated.

12. The method of claim 9 wherein the 1,2-dibromo-2,4-dicyanobutane and dodecylguanidine hydrochloride are applied separately to the article being treated.

13. The method of claim 9 wherein said synergistic antimicrobial composition has a concentration of at least 0.1 ppm.

* * * * *

UNITED STATES PATENT AND TRADEMARK OFFICE
CERTIFICATE OF CORRECTION

PATENT NO. :   5,700,834

DATED       :   December 23, 1997

INVENTOR(S):   Stinavage

It is certified that errors appears in the above-identified patent and that said Letters Patent should be corrected as shown below:

Column 13, Table 8, 4th column, 3rd line from bottom, number "62.4" should be --62.5--.

Signed and Sealed this

Fourteenth Day of December, 1999

*Attest:*

Q. TODD DICKINSON

*Attesting Officer*    *Acting Commissioner of Patents and Trademarks*